(12) United States Patent
Einbond et al.

(10) Patent No.: US 9,801,844 B2
(45) Date of Patent: Oct. 31, 2017

(54) METHODS AND COMPOSITIONS FOR THE TREATMENT OF CANCER

(71) Applicants: Linda S. Einbond, Crestwood, NY (US); Stephen Redenti, New York, NY (US)

(72) Inventors: Linda S. Einbond, Crestwood, NY (US); Stephen Redenti, New York, NY (US)

(73) Assignee: The Research Foundation of the City University of New York, New York, NY (US)

( * ) Notice: Subject to any disclaimer, the term of this patent is extended or adjusted under 35 U.S.C. 154(b) by 334 days.

(21) Appl. No.: 13/902,493

(22) Filed: May 24, 2013

(65) Prior Publication Data
US 2013/0315983 A1 Nov. 28, 2013

Related U.S. Application Data

(60) Provisional application No. 61/651,339, filed on May 24, 2012.

(51) Int. Cl.
| | |
|---|---|
| A61K 31/216 | (2006.01) |
| A61K 9/127 | (2006.01) |
| A61K 31/12 | (2006.01) |
| A61K 36/53 | (2006.01) |
| A61K 36/9066 | (2006.01) |
| A61K 45/06 | (2006.01) |

(52) U.S. Cl.
CPC .......... *A61K 31/216* (2013.01); *A61K 9/127* (2013.01); *A61K 31/12* (2013.01); *A61K 36/53* (2013.01); *A61K 36/9066* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 5,256,700 | A * | 10/1993 | Aeschbach et al. | 514/732 |
| 2006/0067998 | A1 * | 3/2006 | Kurzrock et al. | 424/450 |
| 2007/0142346 | A1 * | 6/2007 | Johnson | A61K 31/395 514/183 |
| 2009/0186078 | A1 * | 7/2009 | Kliche | A61K 9/127 424/450 |

FOREIGN PATENT DOCUMENTS

WO  WO-2008-024485  * 2/2008

OTHER PUBLICATIONS

Cheung S, Anti proliferative and antioxidant properties of rosemary Rosmarinus officinalis, Oncology Reports, 17, 2007, 1525-31.*
Rowe D, Modulation of the BRCA1 protein and inductin of apoptosis in triple negative breast cancer cell lines by the polyphenolic compund curcumin, Breast Cancer: Basic and Clinical Research, 2009, 3, 61-75.*
Tamaki, Y. et al. Activated glutathione metabolism participates in protective effects of carnosic acid against oxidative stress in neuronal HT22 cells. Planta Med. May 2010 ; 76(7):683-8.
Takahashi, T. et al. Carnosic acid and carnosol inhibit adipocyte differentiation in mouse 3T3-L1 cells through induction of phase2 enzymes and activation of glutathione metabolism. Biochem Biophys Res Commun. May 8, 2009; 382(3):549-54.
Narayanan, N. K. et al. Liposome encapsulation of curcumin and resveratrol in combination reduces prostate cancer incidence in PTEN knockout mice. Int J Cancer. Jul. 1, 2009; 125(1):1-8.
Sun, D. et al. A novel nanoparticle drug delivery system: the anti-inflammatory activity of curcumin is enhanced when encapsulated in exosomes. Mol Ther. Sep. 2010; 18(9):1606-14.
Pesakhov, S. et al. Distinct combinatorial effects of the plant polyphenols curcumin, carnosic acid, and silibinin on proliferation and apoptosis in acute myeloid leukemia cells. Nutr Cancer. 2010; 62(6):811-24.

* cited by examiner

*Primary Examiner* — Frederick Krass
*Assistant Examiner* — Celeste A Roney
(74) *Attorney, Agent, or Firm* — Burns & Levinson LLP; Orlando Lopez; Janine M. Susan

(57) ABSTRACT

The invention provides compositions with low toxicity and high bioavailability for treating cancer or for inhibiting the development of cancer.

2 Claims, 9 Drawing Sheets

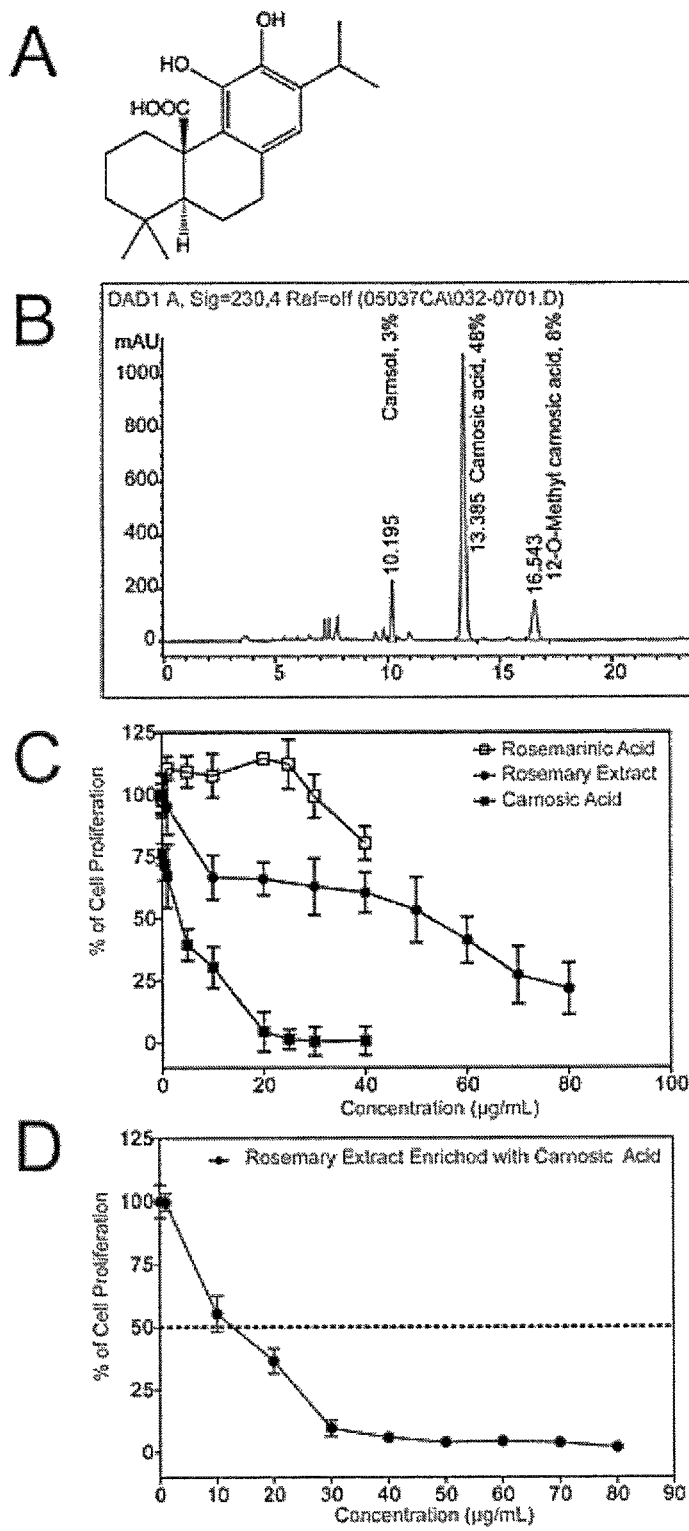
Figs. 1A-D

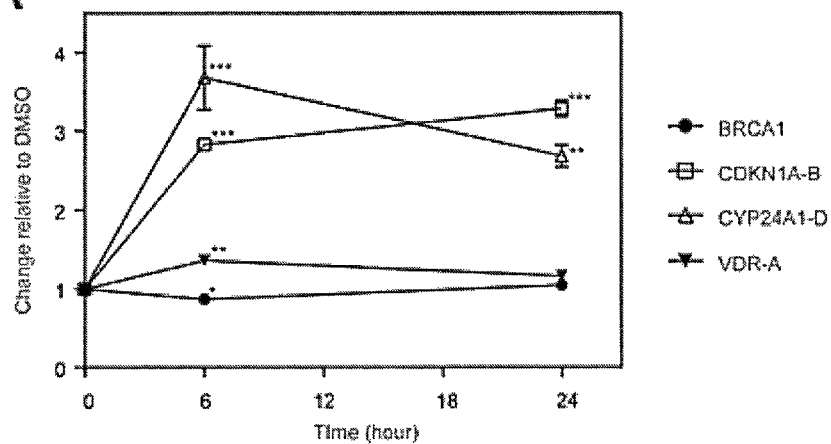
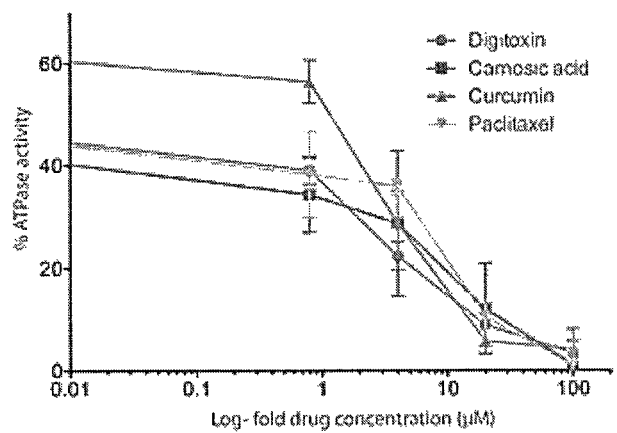
Figs. 3A-B

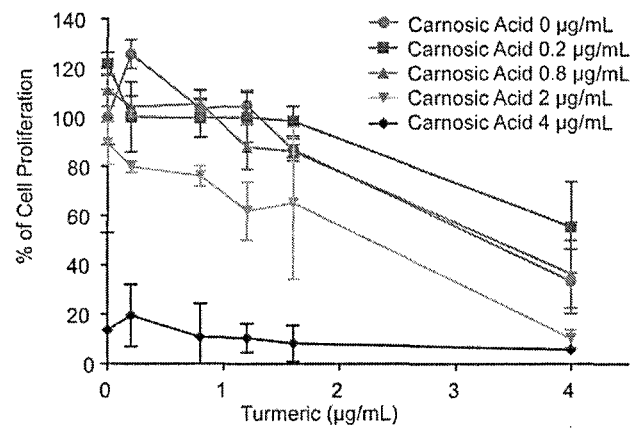
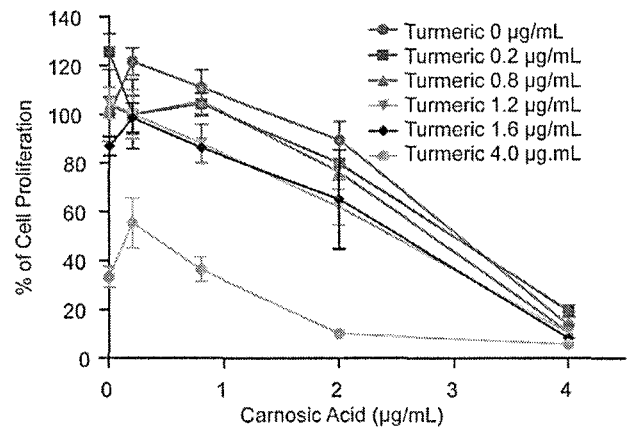
Figs. 4A-B

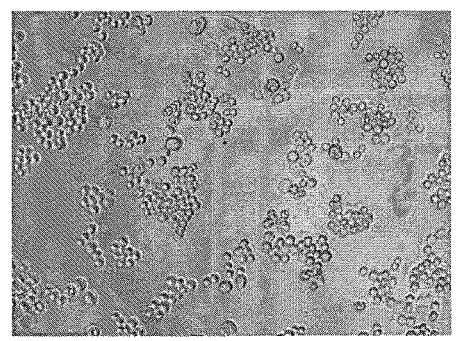
Fig. 5A (Control)
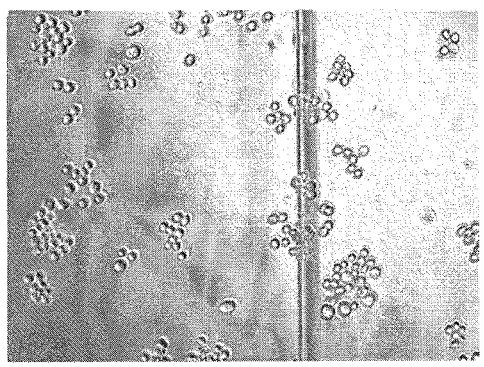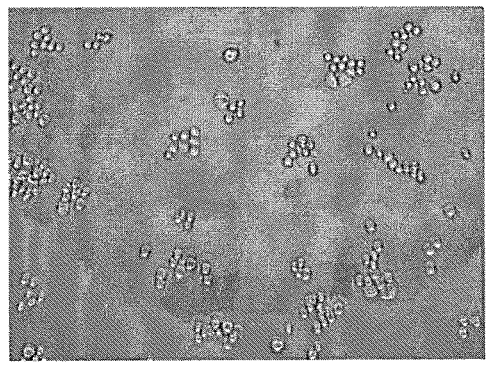
Fig. 5B (0.5 ug/ml Carnosic Acid)     Fig. 5C (0.5 ug/ml Liposome-Carnosic Acid)

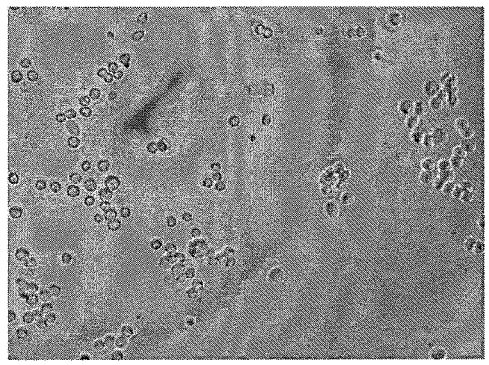
Fig. 5D (5 ug/ml Carnosic Acid)
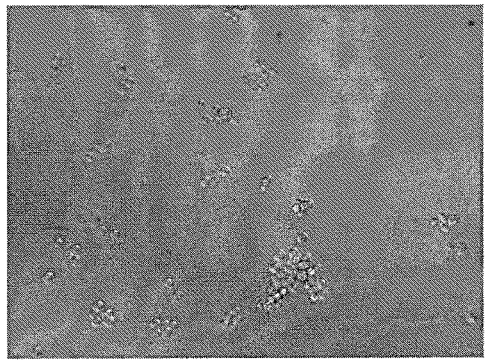
Fig. 5E (5 ug/ml Liposome-Carnosic Acid)
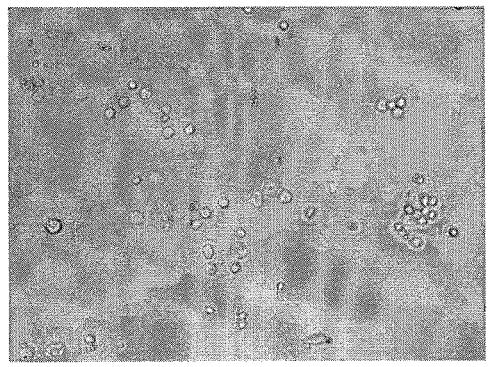
Fig. 5F (10 ug/ml Carnosic Acid)
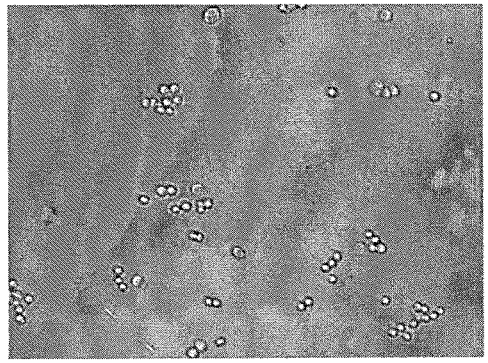
Fig. 5G (10 ug/ml Liposome-Carnosic Acid)
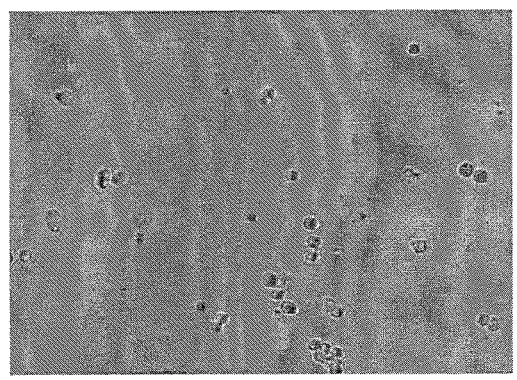
Fig. 5H (20 ug/ml Carnosic Acid)
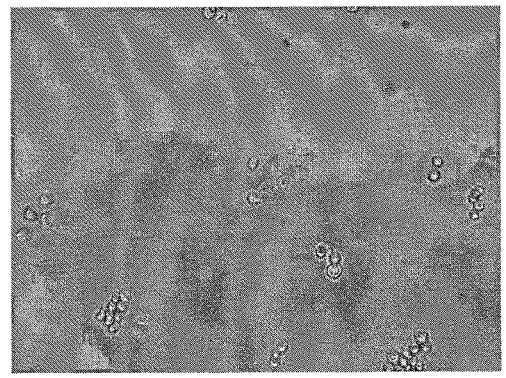
Fig. 5I (20 ug/ml Liposome-Carnosic Acid)

SEM Analysis of Cell derived exosomes and microparticels. Total MV populations isolated from cells include a heterogenous population of spheroid vesicles ranging in size from 30-300nM.

SEQUENCE LISTING

```
<160> NUMBER OF SEQ ID NOS: 8

<210> SEQ ID NO 1
<211> LENGTH: 19
<212> TYPE: DNA
<213> ORGANISM: Homo sapiens

<400> SEQUENCE: 1
agcagcatct gggtgtgag                                              19

<210> SEQ ID NO 2
<211> LENGTH: 21
<212> TYPE: DNA
<213> ORGANISM: Homo sapiens

<400> SEQUENCE: 2
atgttgcatg gtatccctct g                                           21

<210> SEQ ID NO 3
<211> LENGTH: 23
<212> TYPE: DNA
<213> ORGANISM: Homo sapiens

<400> SEQUENCE: 3
agtgcagatt tcctttgtga cat                                         23

<210> SEQ ID NO 4
<211> LENGTH: 21
<212> TYPE: DNA
<213> ORGANISM: Homo sapiens

<400> SEQUENCE: 4
actgtttgct gtcgtttcca c                                           21

<210> SEQ ID NO 5
<211> LENGTH: 20
<212> TYPE: DNA
<213> ORGANISM: Homo sapiens

<400> SEQUENCE: 5
```

```
-continued agcatccaaa aggtcattgg                                          20

<210> SEQ ID NO 6
<211> LENGTH: 20
<212> TYPE: DNA
<213> ORGANISM: Homo sapiens

<400> SEQUENCE: 6
gtcgtccatg gtgaaggact                                          20

<210> SEQ ID NO 7
<211> LENGTH: 20
<212> TYPE: DNA
<213> ORGANISM: Homo sapiens

<400> SEQUENCE: 7
gcctggactg ttttctctcg                                          20

<210> SEQ ID NO 8
<211> LENGTH: 20
<212> TYPE: DNA
<213> ORGANISM: Homo sapiens

<400> SEQUENCE: 8
attcagcatt gtgggaggag                                          20
```

METHODS AND COMPOSITIONS FOR THE TREATMENT OF CANCER

CROSS-REFERENCE TO RELATED APPLICATIONS

This application claims priority to U.S. Provisional Application No. 61/651,339 filed May 24, 2012 and entitled GROWTH INHIBITORY EFFECTS OF NANOPARTICLES CONTAINING CARNOSIC ACID OR RELATED COMPOUNDS, the entire contents of which are incorporated herein by reference for all purposes.

BACKGROUND OF THE INVENTION

Significant advances have been made in the early detection and treatment of breast cancer. Nevertheless, it is still the most common cancer and the second leading cause of cancer death among women in the U.S. The use of current chemopreventive agents, such as tamoxifen and raloxifene, has been limited by toxicity; in addition, they do not reduce the risk of ER negative breast cancer, which represents about one-third of invasive breast cancers and the more aggressive triple negative tumors.

Colon cancer, among other cancers, is a multifactor disease.

Breast cancer and colorectal cancer have been associated with mutations in 189 genes (average of 11 per tumor) (Liby et al., 2007).

There is an imperative need for agents with low toxicity for treating and inhibiting the development of breast cancer, colon cancer and other cancers. The optimal treatment for cancer most likely requires an agent or combination of agents that can correctly target multiple pathways (bioavailability) with minimal toxicity.

Rosemary contains multiple components including carnosic acid (CA), rosmarinic acid, carnosol (CS), caffeic acid, and ursolic acid, which contribute to the biological activity of rosemary and could provide effective synergy. Whole extracts and purified components isolated from rosemary have been shown to inhibit the in vitro and in vivo growth of breast cancer cells.

Carnosic acid, a polyphenolic diterpene (FIG. 1A), in particular, has shown anti-inflammatory, chemopreventive, and anticancer activity. In preclinical studies, vitamin D and carnosic acid showed synergistic growth inhibitory effects in leukemia models. Steiner et al. (Steiner, M, et al., "Carnosic acid inhibits proliferation and augments differentiation of human leukemic cells induced by 1,25-dihydroxyvitamin D3 and retinoic acid," Nutr Cancer 2001; 41:135-44, incorporated by reference herein) found that carnosic acid potentiated the differentiating and antiproliferative effects of 1,25D3 in human myeloid leukemia cell lines HL60 and U937. Danilenko et al. (Danilenko, M. et al., "Carnosic acid and promotion of monocytic differentiation of tHL60-G cells initiated by other agents," J Natl Cancer Inst. 2001; 93:1224-33, incorporated by reference herein) demonstrated that carnosic acid increased the expression of the VDR and augmented its DNA binding activity. Carnosic acid and 1,25D3 synergistically activated the Raf-MEK-ERK-p90RSK MAPK cascade in HL60 cell. Treatment of human myeloid leukemia cells with carnosic acid resulted in a decrease in the intracellular levels of reactive oxygen species (ROS). Moreover, combined treatment of leukemia-bearing mice with a vitamin D analog and rosemary extract resulted in normalization of white blood cell and differential counts and increased survival compared to untreated mice.

Carnosic acid has also been shown to exhibit synergy with curcumin. In KO and HL-60 human AML cells, nontoxic combinations of curcumin and CA resulted in synergistic growth inhibitory effects and significant apoptotic cell death involving the extrinsic and intrinsic apoptotic pathways. It is important that these agents did not alter the viability of normal human fibroblasts or proliferating and nonproliferating blood cells.

Recent studies pertain to the mode of action of CA and CS. Using microarray analysis, CA and CS have been shown to activate the ARE and stimulate glutathione metabolism, which inhibited the differentiation of mouse preadiocytes 3T3-11 cells to adipocyte. Thus CA may have potential to treat obesity related conditions. Further gene expression studies indicated that CA and CS protect cortical neurons (HT22 cells) by activating the Keap1/Nrf2 pathway, which induces phase 2 enzymes and subsequently enzymes involved in glutathione metabolism. In addition, CA has been shown to inhibit the function of the human drug efflux transporter P-glycoprotein (MDR1, ABCB1) and multidrug resistance protein 1 (MRP1, ABCC1).

BRIEF SUMMARY OF THE INVENTION

The present invention overcomes the drawbacks of prior art compositions and methods and is directed to compositions with low toxicity and high bioavilability for treating cancer or for inhibiting the development of cancer.

In one aspect the invention relates to compositions of matter for treating cancer or for inhibiting the development of cancer. In one embodiment, the invention includes compositions of liposomes or exosomes and at least one component of rosemary extract. The component of rosemary extract can be carnosic acid, rosmarinic acid, camosol, 12-O-methyl carnosic acid, carnosic diphenol, camphor, caffeic acid, 3,4-dihydroxyphenyllactic acid, ursolic acid, betulinic acid, rosmaridiphenol, rosmanol or combinations thereof. In a preferred embodiment, the component of rosemary extract is carnosic acid.

In another embodiment, the invention includes compositions of liposomes or exosomes, at least one component of rosemary extract and at least one component of turmeric. The component of rosemary extract can be carnosic acid, rosmarinic acid, carnosol, 12-O-methyl carnosic acid, carnosic diphenol, camphor, caffeic acid, 3,4-dihydroxyphenyllactic acid, ursolic acid, betulinic acid, rosmaridiphenol, rosmanol or combinations thereof. In a preferred embodiment, the component of rosemary extract is carnosic acid. The component of turmeric can be curcumin, desmethoxycurcumin, bis-desmethoxycurcumin or combinations thereof. In a preferred embodiment, the component of turmeric is curcumin.

In other embodiments, the invention includes compositions of liposomes or exosomes, at least one component of rosemary extract and, optionally, a chemopreventitive agent or a chemotherapy agent. In other embodiments, the invention includes compositions of liposomes or exosomes, at least one component of rosemary extract, at least one component of turmeric and, optionally, a chemopreventitive agent or a chemotherapy agent. In some particular embodiments, the chemopreventitive agent or chemotherapy agent is paclitaxel, doxorubicin, 5-FU, herceptin, tamoxifen, sulindac sulfide or combinations thereof In the various embodiments described herein, the liposomes can be made up of one or more lipids. The lipids can be 1,2-dioleoyl-sn-glycero-3-phosphocholine (DOPC), 1,2-dioleoyl-sn-glycero-3-phosphoethanolamine (DOPE), phosphoethanolamine (PE), 1,2-dimyristoyl-sn-glycero-3-phosphocholine (DMPC), 1,2-dimyristoyl-sn-glycero-3-phosphoglycerol (DMPG) or combinations thereof.

In the various embodiments described herein, the ratio of total amount of lipid by weight to total amount of active ingredient(s) (i.e. component of rosemary extract, component of turmeric, chemopreventitive agent, chemotherapy agent or combinations thereof) by weight is about 10:1 to about 4:1.

Another aspect of the invention relates to methods of treating cancer or inhibiting development of cancer by administering a pharmaceutically effective amount of a composition of liposomes or exosomes and at least one component of rosemary extract. The cancer can be carcinoma, lymphoma, blastoma, medulloblastoma, retinoblastoma, sarcoma, liposarcoma, synovial cell sarcoma, neuroendocrine tumors, carcinoid tumors, gastrinoma, islet cell cancer, mesothelioma, schwannoma, acoustic neuroma, meningioma, adenocarcinoma, melanoma, leukemia, lymphoid malignancies, squamous cell cancer, epithelial squamous cell cancer, lung cancer, small-cell lung cancer (SCLC), non-small cell lung cancer (NSCLC), adenocarcinoma of the lung, squamous carcinoma of the lung, cancer of the peritoneum, hepatocellular cancer, gastric cancer, stomach cancer, gastrointestinal cancer, pancreatic cancer, glioblastoma, cervical cancer, ovarian cancer, liver cancer, bladder cancer, hepatoma, breast cancer, metastatic breast cancer, colon cancer, rectal cancer, colorectal cancer, endometrial carcinoma, uterine carcinoma, salivary gland carcinoma, kidney cancer, renal cancer, prostate cancer, vulval cancer, thyroid cancer, hepatic carcinoma, anal carcinoma, penile carcinoma, testicular cancer, esophagael cancer, tumors of the biliary tract, head and neck cancer, and triple-negative metastatic breast cancer. In one embodiment, the cancer is colon cancer. In another embodiment the cancer is breast cancer. In yet another embodiment, the cancer is ovarian cancer.

Another aspect of the invention relates to methods of treating breast cancer by administering a pharmaceutically effective amount of a composition of carnosic acid and turmeric/curcumin. The breast cancer can be ER negative breast cancer or triple negative metastatic breast cancer. The composition of carnosic acid and turmeric/curcumin synergistically inhibits growth of human breast cancer cells.

Another aspect of the invention relates to methods of inhibiting the activity of Na$^+$-K$^+$-ATPase by administering a pharmaceutically effective amount of a composition of curcumin, carnosic acid, paclitaxel, digitoxin or combinations thereof.

BRIEF DESCRIPTION OF THE DRAWINGS

FIG. 1A depicts the structure of carnosic acid;

FIG. 1B is a HPLC chromatogram of rosemary extract enriched for carnosic acid;

FIG. 1C is a graph of growth inhibitory activity of carnosic acid, rosmarinic acid, and rosemary extract enriched for rosmarinic acid (55%; Naturex) on the growth of MDA-MB-453 human breast cancer cells;

FIG. 1D is a graph of growth inhibitory activity of rosemary extract enriched in carnosic acid (50%) on the growth of MDA-MB-453 human breast cancer cells;

FIG. 3A is a graph of real-time RT-PCR of MIDA-MB-468 breast cancer cells after treating with carnosic acid for 6 or 24 h. (*, p<0.05; , p<0.01; *p<0.001);

FIG. 3B is a graph of inhibition of Na+-K+-ATPase activity in response to increasing concentrations of agents;

FIGS. 4A and B are graphs of synergistic combinations of carnosic acid (A) and curcumin (B) on MDA-MB-468 human breast cancer cells;

FIGS. 5A-I are photographs of microscope images of MDA-MB-453 cells treated with Carnosic Acid or Liposome-Carnosic Acid for 96 hours;

DETAILED DESCRIPTION OF THE INVENTION

Figure 2A:
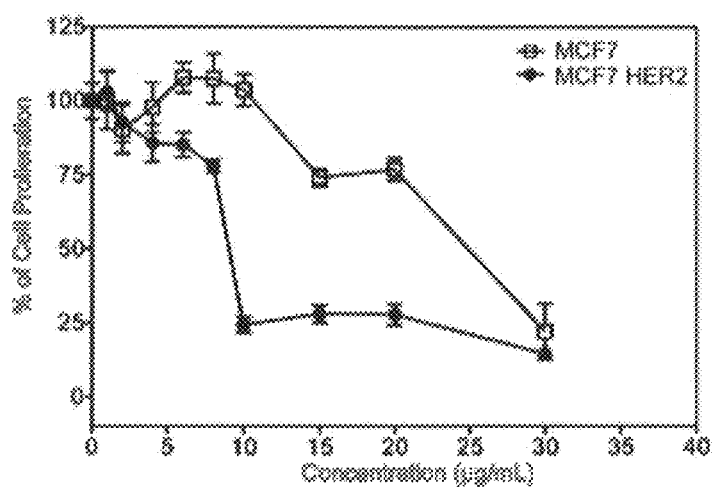
FIG. 2A is a graph of growth inhibitory activity of carnosic acid from rosemary on the growth of the genetically matched pair of cells MCF7 and MCF7(Her2)

Problems with currently existing treatments for cancer include toxicity and lack of bioavailability. Most anti-cancer drugs are not selective for tumor cells over normal cells resulting in unacceptable levels of toxicity. In addition the efficacy of anti-cancer drugs is often limited by its bioavailability.

The toxicity problem can be overcome by using diterpenes and related constituents from the herb rosemary (rosemary/carnosic acid) (and natural phenol antioxidant carboxylic acid such as rosmarinic acid) in combination with chemopreventive or chemotherapy agents.

Examples of chemotherapeutic agents include Erlotinib (TARCEVA, Genentech/OSI Pharm.), Bortezomib (VELCADE, Millennium Pharm.), Fulvestrant (FASLODEX, AstraZeneca), Sutent (SU11248, Pfizer), Letrozole (FEMARA, Novartis), Imatinib mesylate (GLEEVEC, Novartis), PTK787/ZK 222584 (Novartis), Oxaliplatin (Eloxatin, Sanofi), 5-FU (5-fluorouracil), Leucovorin, Rapamycin (Sirolimus, RAPAMUNE, Wyeth), Lapatinib (TYKERB, GSK572016, Glaxo Smith Kline), Lonafarnib (SCH 66336), Sorafenib (BAY43-9006, Bayer Labs), and Gefitinib (IRESSA, AstraZeneca), AG1478, AG1571 (SU 5271; Sugen), alkylating agents such as thiotepa and CYTOXAN cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (Angew Chem. Intl. Ed. Engl. (1994) 33:183-186);

dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamniprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE (Cremophor-free), albumin-engineered nanoparticle formulations of paclitaxel (American Pharmaceutical Partners, Schaumberg, Ill.), and TAXOTERE (doxetaxel; Rhone-Poulenc Rorer, Antony, France); chloranmbucil; GEMZAR (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE (vinorelbine); trone; teniposide; edatrexate; daunomycin; aminopterin; capecitabine (XELODA ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX; tamoxifen citrate), raloxifene, droloxifene, 4-hydroxytamoxifen, trioxifene, keoxifene, LY117018, onapristone, and FARESTON (toremifine citrate); (ii) aromatase inhibitors that inhibit the enzyme aromatase, which regulates estrogen production in the adrenal glands, such as, for example, 4(5)-imidazoles, aminoglutethimide, MEGASE (megestrol acetate), AROMASIN (exemestane; Pfizer), formestanie, fadrozole, RIVISOR (vorozole), FEMARA (letrozole; Novartis), and ARIMIDEX (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME and HER2 expression inhibitors; (viii) vaccines such as gene therapy vaccines, for example, ALLOVECTIN, LEUVECTIN, and VAXID; PROLEUKIN rIL-2; a topoisomerase 1 inhibitor such as LURTOTECAN; ABARELIX rmRH; (ix) anti-angiogenic agents such as bevacizumab (AVASTIN, Genentech); and (x) pharmaceutically acceptable salts, acids and derivatives of any of the above. Other anti-angiogenic agents include MMP-2 (matrix-metalloproteinase 2) inhibitors, MMP-9 (matrix-metalloproteinase 9) inhibitors, COX-II (cyclooxygenase II) inhibitors, and VEGF receptor tyrosine kinase inhibitors. Examples of such useful matrix metalloproteinase inhibitors that can be used in combination with the present compounds/compositions are described in WO 96/33172, WO 96/27583, EP 818442, EP 1004578, WO 98/07697, WO 98/03516, WO 98/34918, WO 98/34915, WO 98/33768, WO 98/30566, EP 606,046, EP 931,788, WO 90/05719, WO 99/52910, WO 99/52889, WO 99/29667, WO 99/07675, EP 945864, U.S. Pat. No. 5,863,949, U.S. Pat. No. 5,861,510, and EP 780,386, all of which are incorporated herein in their entireties by reference. Examples of VEGF receptor tyrosine kinase inhibitors include 4-(4-bromo-2-fluoroanilino)-6-methoxy-7-(1-methylpiperidin-4-ylmethoxy)qu- -inazoline (ZD6474; Example 2 within WO 01/32651), 4-(4-fluoro-2-methylindol-5-yloxy)-6-methoxy-7-(3-pyrrolidin-1-yl-propoxy)-1-quinazoline (AZD2171; Example 240 within WO 00/47212), vatalanib (PTK787; WO 98/35985) and SU11248 (sunitinib; WO 01/60814), and compounds such as those disclosed in PCT Publication Nos. WO 97/22596, WO 97/30035, WO 97/32856, and WO 98/13354).

Other examples of chemotherapeutic agents include inhibitors of PI3K (phosphoinositide-3 kinase), such as those reported in Yaguchi et al (2006) Jour. of the Nat. Cancer Inst. 98(8):545-556; U.S. Pat. No. 7,173,029; U.S. Pat. No. 7,037,915; U.S. Pat. No. 6,608,056; U.S. Pat. No. 6,608,053; U.S. Pat. No. 6,838,457; U.S. Pat. No. 6,770,641; U.S. Pat. No. 6,653,320; U.S. Pat. No. 6,403,588; WO 2006/046031; WO 2006/046035; WO 2006/046040; WO 2007/042806; WO 2007/042810; WO 2004/017950; US 2004/092561; WO 2004/007491; WO 2004/006916; WO 2003/037886; US 2003/149074; WO 2003/035618; WO 2003/034997; US 2003/158212; EP 1417976; US 2004/053946; JP 2001247477; JP 08175990; JP 08176070; U.S. Pat. No. 6,703,414; and WO 97/15658, all of which are incorporated herein in their entireties by reference. Specific examples of such PI3K inhibitors include SF-1126 (PI3K inhibitor, Semafore Pharmaceuticals), BEZ-235 (PI3K inhibitor, Novartis), XL-147 (PI3K inhibitor, Exelixis, Inc.).

The terms "cancer" and "cancerous" refer to or describe the physiological condition in mammals that is typically characterized by unregulated cell growth. Included in this definition are benign and malignant cancers. By "early stage cancer" or "early stage tumor" is meant a cancer that is not invasive or metastatic or is classified as a Stage 0, 1, or II cancer. Examples of cancer include, but are not limited to, carcinoma, lymphoma, blastoma (including medulloblastoma and retinoblastoma), sarcoma (including liposarcoma and synovial cell sarcoma), neuroendocrine tumors (including carcinoid tumors, gastrinoma, and islet cell cancer), mesothelioma, schwannoma (including acoustic neuroma), meningioma, adenocarcinoma, melanoma, and leukemia or lymphoid malignancies. More particular examples of such cancers include squamous cell cancer (e.g. epithelial squamous cell cancer), lung cancer including small-cell lung cancer (SCLC), non-small cell lung cancer (NSCLC), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer (including metastatic breast cancer), colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular carcinoma, esophagael cancer, tumors of the biliary tract, as well as head and neck cancer. In some embodiments, the cancer is triple-negative metastatic breast cancer, including any histologically confirmed triple-negative (ER−, PR−, HER2−) adenocarcinoma of the breast with locally recurrent or metastatic disease, e.g., where the locally recurrent disease is not amenable to resection with curative intent.

The bioavailability problem can be overcome by using nanoparticles. The diterpene carnosic acid or related components (e.g., identified from rosemary such as rosmarinic acid, carnosol, 12-O-methyl carnosic acid, carnosic diphenol, camphor, caffeic acid, 3,4-dihydroxyphenyllactic acid, ursolic acid, betulinic acid, rosmaridiphenol, rosmanol or combinations thereof), either alone or in combination with other substances including turmeric or components thereof (e.g, curcumin, desmethoxycurcumin, bis-desmethoxycurcumin), chemopreventive agents and/or chemotherapy agents can be incorporated into nanoparticles, liposomes, or exosomes in order to provide significant non-toxic anticancer effects.

Nanoparticles can be used in free form where efficacy is limited by solubility. Nanoparticles can be used in other forms (e.g., membrane-bound Nanoparticles), to significantly increase the solubility and stability in vitro and bioavailability in vivo. Additionally, the liposomes or exosomes can be formulated as nanoparticles.

While studies point to CA as one bioactive component of rosemary, studies of rosemary extract are nevertheless essential. Since cancer affects multiple genes, the optimal treatment may require mixtures, including extracts containing several components that can target multiple pathways.

Rosemary/carnosic acid and/or turmeric/curcumin can have added health benefits, such as for other cancers. In addition, the one or more components of rosemary extract and the one or more components of turmeric alone or in combination can be used as anti-oxidants or anti-inflammatories, or for their cardiovascular effects or neurological effects. In addition, the one or more components of the rosemary extract and/or turmeric can be administered with additional substances. Also, the one or more components of rosemary extract and/or turmeric can be formulated as nanoparticles or within liposomes or exosomes when being used as anti-oxidants or anti-inflammatories, or for their cardiovascular effects or neurological effects.

Materials

All solvents and reagents were reagent grade; H2O was distilled and deionized. CA, curcumin, digitoxin (Sigma, St. Louis, Mo.), rosemary extract (Naturex #141804: CA 50%, Naturex: 55% rosmarinic acid) and turmeric (Naturex #140500; standard 95% curcuminoids) were dissolved in dimethylsulfoxide (DMSO) (Sigma; St. Louis, Mo.) prior to addition to cell cultures.

Plant Materials: Extraction and Isolation Procedures

Rosemary contains a number of potentially biologically active compounds, including antioxidants carnosic acid (CA) and rosmarinic acid (RA). Other chemical compounds include carnosol (CS), 12-O-methyl carnosic acid, carnosic diphenol, camphor, caffeic acid, 3,4-dihydroxyphenyllactic acid, ursolic acid, betulinic acid, rosmaridiphenol and rosmanol.

Naturex, Inc. (South Hackensack, N.J.) generously provided rosemary extract (Number: 141804; CA 50%). To prepare the rosemary extract, rosemary was collected from Morocco. By HPLC analysis, the main components of the extract are CA (48%), 12-O-methyl CA (8%), and CS (3%) (FIG. 1B). The procedure to prepare the extract is as follows: rosemary leaf was first ground into small particles, extracted with acetone at room temperature, filtered and concentrated under reduced pressure, then treated with acid and base. The acid insoluble substances, which include CA and CS, as well as carnosic derivatives, were precipitated, separated from liquid and dried in a vacuum oven to obtain the final product.

Cell Culture

MDA-MB-453 (ER negative, Her2 overexpressing), MDA-MB-468 (triple negative) and MCF7 (ER positive, Her2 low) cells, HT29 (p53 positive human colon cancer cells) (ATCC, Manassas, Va.) were grown in Dulbecco's Modified Eagle's medium (DMEM) (Gibco BRL Life Technologies, Inc., Rockville, Md.) containing 10% (v/v) fetal bovine serum (FBS) (Gibco BRL) at 37° C., 5% C02. SUM 149 (Her2 overexpressing, ER low) (the gift of Dr. R. Parsons, Columbia University Medical Center, New York, N.Y.) were cultivated in Ham's F-12 medium with 10% FBS. MCF7 and MCF7/Her2-18 (MCF7 cells transfected with a full length Her2 cDNA coding region, 45-fold increase Her2) were the kind gift of Dr. Dennis Slamon (Los Angeles, Calif.). These cells were maintained in RPMI supplemented with 10% FBS plus glutamine (1%) and PSF (1%) (Gibco, Rockville Md.).

The HT29 cells were maintained in McCoy's Media containing 10% (v/v) fetal bovine serum (FBS) (Gibco BRL) at 37° C., 5% C02.

Cell Growth

MTT assay: the MTT {3-(4,5-dimethyl-2-thiazol)-2,5-diphenyl-2H tetrazolilum bromide} (Dojindo; Tokyo, Japan) cell proliferation assay system (Roche Diagnostic, Mannheim, Germany) was used to determine the sensitivity of the various cell lines to agents. Cells were seeded at 1×104 cells/well in 96-well plates and allowed to attach for 24 h. The medium was replaced with fresh medium containing DMSO or compound. The cells were treated for 96 or 120 h, after which they were incubated with MTT reagents and the absorbance read at 650 and 575 nm. For cell growth assays, the data are expressed as mean+/−standard deviation. Control and treated cells were compared using the student's t-test ($p<0.05$).

The Effects of an Extract and Purified Components from Rosemary on Breast Cancer Cell Growth.

To identify the components of rosemary responsible for the growth inhibitory effect, the effects of the putative active components CA and rosmarinic acid (obtained from Sigma, St. Louis) were compared to the effects of rosemary extract, enriched for rosmarinic acid (55%). The respective IC50 values, the concentration that caused 50% inhibition of cell proliferation, by MTT assay, were; CA: 3 µg/ml (7 µM), rosmarinic acid: ~56 µg/ml (~150 µM), rosemary extract enriched for rosmarinic acid (55%; Naturex): 52 µg/ml (FIG. 1C) Thus CA displayed strong growth inhibitory activity on MDA-MB-453 Her2 overexpressing human breast cancer cells, followed by rosemary extract and then rosmarinic acid. To validate these results, the growth inhibitory activity of an extract of rosemary enriched for CA (50%; Naturex number 141804) was tested on MDA-MB-453 cells and was found to possess potent activity (IC50 value: 12 µg/ml) (FIG. 1D).

In addition, the growth inhibitory activity of CA on ER-negative SUM149 and MDA-MB-468 cells was examined. The IC50 values, by MTT assay, were CA: 1.7 µg/ml (5.1 µM) and 2 µg/ml (6.0 µM), respectively. CA is more active than the chemopreventive agents EGCG and resveratrol and about equal to curcumin on MDA-MB-453 cells; the respective IC50 values were: curcumin 2 µg/ml (5.4 µM), resveratrol 4 µg/ml (17.5 µM), and EGCG ~100 µg/ml (218 µM).

The Role of Her2

To determine the role of Her2 in the action of CA, the effect of CA on the genetically matched pair of cells MCF7 (ER positive, Her2 low) and MCF7/Her2-18 (MCF7 cells transfected with a full length Her2 cDNA coding region, 45-fold increase Her2) was examined. The IC50 values were 25 µg/ml (75 µM) and 9 µg/ml (27 µM), respectively, indicating that sensitivity correlates with Her2 expression (FIG. 2A).

The Effects of Rosemary/Carnosic Acid on Cell Cycle Kinetics.

For cell cycle analysis the cells were plated ($3 \times 10^5$) onto 6 cm dishes and allowed to attach for 24 h. Then the medium was replaced with DMEM containing 10% FBS and DMSO or agents. After 48 h, the cells were analyzed by DNA flow cytometry.

To examine the effects of rosemary on the cell cycle, MDA-MB-453 human breast cancer cells were treated with rosemary extract enriched for CA (50%) at 40 or 80 µg/ml and purified CA at 10, 20 or 40 µg/ml for 48 h. The cells were then stained with propidium iodide and the stained cells were analyzed by DNA flow cytometry (Table 1).

TABLE 1

Effects of rosemary extract enriched for carnosic acid (50%) and purified carnosic acid on the distribution of cells in the cell cycle at 48 h.

| Treatment | % of Cells | | | |
|---|---|---|---|---|
| | G1 | S | G2 | Sub G1 |
| DMSO | 51.2 | 28.9 | 10.5 | 1.4 |
| Carnosic acid 10 ug/ul | 51.2 | 31.2 | 11.8 | 1.5 |
| Carnosic acid 20 ug/ul | 71.9 | 15.3 | 9.1 | 1.7 |
| Carnosic acid 40 ug/ul | 50.8 | 28.9 | 13.9 | 1.6 |
| Rosemary ext 40 ug/ul | 56.96 | 23.3 | 13.9 | 0.4 |
| Rosemary ext 80 ug/ul | 49.3 | 22.2 | 18 | 0.5 |

MDA-MB-453 cells were treated with 0, 10, 20, or 40 µg/ml of carnosic acid or 40, 80 µg/ml of rosemary extract (carnosic acid: 50%), and analyzed at 48 hr by DNA flow cytometry. The values indicate the % of cells in the cell cycle phases.

Treatment with rosemary extract enriched for CA at 40 µg/ml induced an increase in the percent cells in the G1 phase (51.2 to 57.0%) and a concomitant decrease in the percent cells in S phase (28.9 to 23.3%), while the extract at a higher concentration (80 µg/ml) induced an increase in the percent cells in G2 phase (10.5 to 18%). Treatment with CA induced a similar pattern of effects. CA at 10 µg/ml had little effect, at 20 µg/ml induced a pronounced increase in the percent cells in G1 (51.2 to 71.9%) and at 40 µg/ml induced a small increase in G2.

Gene Expression Analysis

MDA-MB-468 cells were treated with 5 µg/mL (15 µM) or 20 µg/mL of CA for 6 or 24 h. RNA was isolated using methods known in the art. Total cellular RNA was extracted using Trizol (Invitrogen; Carlsbad, Calif.) according to the manufacturer's protocol with minor modifications, and then purified twice with Qiagen's RNeasy column. Total RNA (8 µg) was reverse transcribed with T7-(dT)24 primer and Super Script III reverse transcriptase (Invitrogen).

Microarray analysis was performed using methods known in the art. Labeled cDNA was generated from MDA-MB-468 cells and hybridized to Affymetrix U1332A genome arrays at Columbia University following standard Affymetrix protocols. Analysis was performed using the AffyLimmaGUI package in the open-source Bioconductor suite.

To determine the primary targets of carnosic acid on triple negative breast cancer, MDA-MB-468 human breast cancer cells were treated with CA at 2 doses, 5 µg/ml (15 µM) and 20 µg/ml, for a short duration, 6 h. After treatment with the lower dose, 5 ug/ml, CA activated the expression of three genes. The genes were involved in glutathione biosynthesis (CYP4F3, GCLC) and transport (SLC7A11) ($p<0.05$). At the higher dose, 20 µg/ml, CA altered 124 genes, $p<0.05$. The ratio of genes activated to suppressed was (102/22=4.6).

The most significant genes {top 40 M (log-fold)} are listed in Table 2. CA activated the expression of genes involved in anti-inflammation (HMOX1), xenobiotic mtabolism (AKR1C2), antioxidant (TNXRD), transport (SLC7A11), apoptosis (GDF15, PHLDA1, DDIT3), glutathione biosynthesis (GCLC, GCLM) and signaling (GRB10) and repressed the expression of inhibitors of transcription (ID3) and cell cycle (CDKN2C) genes.

Figure 2B:
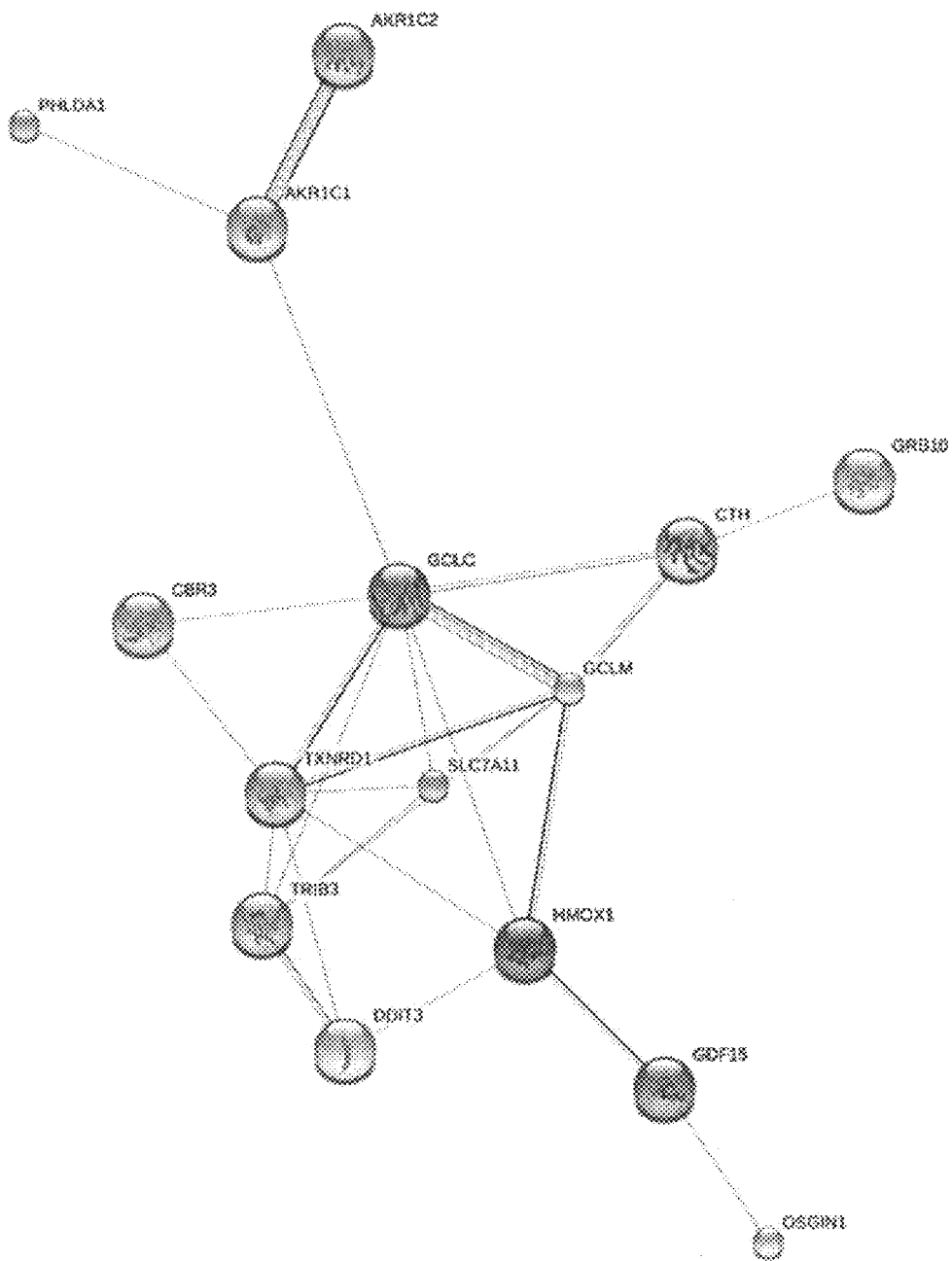
FIG. 2B depicts STRING (Functional Protein Association Networks) analysis of the effects of carnosic acid at 20 µg/ml for 6 h.

The analysis program STRING (Functional Protein Association Networks) (FIG. 2B) was used to examine the interrelations of the genes. The genes at the central hubs of the network were involved in glutathione metabolism (GCLC), redox (TXNRD1) and apoptosis (DDIT3).

TABLE 2

Microarray analysis of differentially expressed genes after treating with carnosic acid (20 µg/ml) for 6 h.

| Function | ID | Gene Symbol | M | P. Value |
|---|---|---|---|---|
| anti-inflammatory | 203665_at | HMOX1 | 6.2079 | 0.0107 |
| oxidoreductase | 211653_x_at | AKR1C2 | 4.1458 | 0.0107 |
| transport | 217678_at | SLC7A11 | 3.9492 | 0.0021 |
| oxidoreductase | 216594_x_at | AKR1C1 | 3.8405 | 0.0145 |

TABLE 2-continued

Microarray analysis of differentially expressed genes
after treating with carnosic acid (20 μg/ml) for 6 h.

| Function | ID | Gene Symbol | M | P. Value |
|---|---|---|---|---|
| transport | 209921_at | SLC7A11 | 3.7330 | 0.0021 |
| apoptosis | 22577_x_at | GDF15/LOC100292463 | 3.2033 | 0.0107 |
| glutathione synthesis | 202922_at | GCLC | 2.5514 | 0.0107 |
| monoxygenase activity | 206515_at | CYP4F3 | 2.4762 | 0.0058 |
| amino acid metabolic process | 217127_at | CTH | 2.3586 | 0.0034 |
|  | 202923_s_at | GCLC | 2.3524 | 0.0043 |
| aldoketoreductase | 206561_s_at | AKR1B10 | 2.3416 | 0.0107 |
|  | 206085_s_at | CTH | 2.3083 | 0.0032 |
| transport | 207528_s_at | SLC7A11 | 2.3041 | 0.0043 |
| transport | 206155_at | ABCC2 | 2.2558 | 0.0101 |
| nucleotide binding | 204411_at | KIF21B | 2.0237 | 0.0043 |
| promote apoptosis | 217996_at | PHLDA1 | 1.9833 | 0.0043 |
| microtubule bundle formation | 210015_s_at | MAP2 | 1.9566 | 0.0101 |
| growth inhibitor | 219475_at | OSGIN1 | 1.9508 | 0.0053 |
| apoptois | 209383_at | DDIT3/NR1H3 | 1.8207 | 0.0043 |
| cytokine activity | 217739_s_at | NAMPT | 1.7329 | 0.0141 |
| redox | 201266_at | TXNRD1 | 1.6785 | 0.0107 |
| signaling | 209409_at | GRB10 | 1.6777 | 0.0053 |
| reductase activity | 218145_at | TRIB3 | 1.6338 | 0.0107 |
| cysteine metabolic process | 203925_at | GCLM | 1.6079 | 0.0107 |
| promote apoptosis | 204286_s_at | PMAIP1 | 1.5443 | 0.0141 |
|  | 217738_at | NAMPT | 1.4857 | 0.0107 |
| metabolic process | 205379_at | CBR3 | 1.4702 | 0.0158 |
| tubulin modification | 203702_s_at | TTLL4 | 1.4497 | 0.0142 |
| nucleotide binding | 209882_at | RIT1 | 1.3792 | 0.0130 |
| potassium ion | 218553_s_at | KCTD15 | 1.3491 | 0.0107 |
|  | 221865_at | C9orf91 | 1.3335 | 0.0145 |
| amino acid transporter | 218041_x_at | SLC38A2 | 1.2613 | 0.0145 |
|  | 220924_s_at | SLC38A2 | 1.2541 | 0.0173 |
| nucleotide binding | 221215_s_at | RIPK4 | −1.2540 | 0.0107 |
| inhibit transcription | 202814_s_at | HEXIM1 | −1.2946 | 0.0107 |
| DNA binding | 201510_at | ELF3 | −1.3391 | 0.0121 |
| aldehyde dehydrogenase | 222168_at | ALDH1A3 | −1.4627 | 0.0107 |
| nucleic acid binding | 213051_at | ZC3HAV1 | −1.5819 | 0.0107 |
| cell cycle | 204159_at | CDKN2C | −1.5843 | 0.0141 |
| inhibit transcription | 207826_s_at | ID3 | −1.9788 | 0.0158 |

Affy-Limma analysis was used to determine the effects of carnosic acid, at a dose of 20 μg/ml and at 6 h on the gene expression pattern in MDA-MB-468 breast cancer cells. Assays were performed as described in the Materials and methods section. Fold change (log) is the mean of the ratio of hybridization signals in carnosic acid treated vs. control treated cells {40 highest M (log-fold) values; p<0.05}.

The Effects of Carnosic Acid on Expression of Specific mRNAs Determined by Real-Time RT-PCR Real-time RT-PCR analysis was performed on 2 technical replicates of at least 2 biological sample replicates.

Real-time quantitative RT-PCR methods were used to determine the nature of the RNA induced by treatment with CA, using the Real Time PCR machine Stratagene MX3005P QPCR System. Primer sequences used in qPCR are listed in Table 2A.

Real-time RT-PCR analysis was performed to examine the mode of action of CA. In MDA-MB-468 cells, CA at 4 μg/ml induced an increase in expression of RNA of the tumor suppressor gene CDKN1A; for MDA-MB-468 cells (6 h: 1.51-logfold; 24 h: 1.61-logfold) (FIG. 3A); for SUM149 cells (6 h: 2.7-logfold). CA had little effect on the expression of the tumor suppressor gene BRCA1. The effect of CA on the expression of the enzyme that initiates the degradation of vitamin D (1,25-dihydroxyvitamin D3) and plays a role in calcium homeostasis was examined, CYP24A1 and a significant increase in expression was seen. Treatment with CA also resulted in a slight increase in expression of the vitamin D receptor at 6 h.

In Table 2A, mRNA sequences were obtained from the public GeneBank database (www.ncbi.nlm.nih.gov), and primers were designed using Primer3software from The Massachusetts Institute of Technology (frodo.wi.mit.edu/cgi-bin/primer3/primer3_www.cgi).

TABLE 2A

Designed primer sequences used in RT-PCR.

| Gene name | Primer direction | Sequence |
|---|---|---|
| BRCA1 | Forward | agcagcatctgggtgtgag (SEQ ID NO: 1) |
|  | Reverse | atgttgcatggtatccctctg (SEQ ID NO: 2) |
| CYP24A1 | Forward | agtgcagatttcctttgtgacat (SEQ ID NO: 3) |
|  | Reverse | actgtttgctgtcgtttccac (SEQ ID NO: 4) |
| VDR | Forward | agcatccaaaaggtcattgg (SEQ ID NO: 5) |
|  | Reverse | gtcgtccatggtgaaggact (SEQ ID NO: 6) |
| CDKN1A | Forward | gcctggactgttttctctcg (SEQ ID NO: 7) |
|  | Reverse | attcagcattgtgggaggag (SEQ ID NO: 8) |

Synergistic Combinations of Carnosic Acid and Curcumin

To determine the Combination Index (CI), cells were treated with all combinations of 4 or 5 concentrations of each of the agents tested and a solvent control. The results of the MTT assay were analyzed for possible synergistic effects using the median effect principle. Variable ratios of drugs were employees and mutually exclusive equations were assumed.

The ability of CA to potentiate the effects of the dietary component curcumin from the spice turmeric on triple negative breast cancer cells was examined. The IC50 values for CA and curcumin alone were 3 µg/ml (9.0 µM) and 2.3 µg/ml (6.2 µM), respectively. Increasing concentrations of CA were combined with increasing concentrations of turmeric/curcumin (FIG. 4A,B). At a dose of CA 2 µg/ml (6 µM), the percent viable cells decreased from 89.4% with CA alone to 79.9% with curcumin 0.2 µg/ml (5.4 µM), to 61.9% with curcumin 1.2 µg/ml (3.3 j±M), to 10.1% with curcumin 4 µg/ml (10.9 µM). Thus curcumin enhances the growth inhibitory effect of CA on MDA-MB-468 triple negative breast cancer cells. The combination indexes for the combination of CA (4.0 µg/ml) and curcumin (1.6 µg/ml) was approximately 0.8, indicating synergy and for CA (2 µg/ml) and curcumin (4 µg/ml) or CA and curcumin both 4 µg/ml was approximately 0.52 or <0.1, respectively, indicating strong synergy.

TABLE 3

Combination index (CI) values for HT29 cells treated with carnosic acid plus turmeric.

| Turmeric (µg/ml) | Carnosic acid (µg/ml) | | | |
|---|---|---|---|---|
| | 0.2 | 0.8 | 2.0 | 4.0 |
| 0.2 | 2.3 (− −) | 2.0 (− −) | 1.66 (− −) | 0.97 (+ −) |
| 0.8 | 2.27 (− −) | 1.96 (− −) | 1.63 (− −) | 0.93 (+ −) |
| 1.2 | 2.13 (− −) | 1.83 (− −) | 1.50 (− −) | 0.8 (+ +) |
| 1.6 | 2.15 (− −) | 1.85 (− −) | 1.51 (− −) | 0.82 (+) |
| 4 | 1.45 (− −) | 1.15 (−) | 0.81 (+) | 0.12 (+ + +) |

>1.3 (− −), antagonism; 1.1-1.3 (−), moderate antagonism; 0.9-1.1 (+ −), additive effect; 0.8-0.9 (+), slight synergism; 0.6-0.8 (+ +), moderate synergism; <0.6 (+ + +), strong synergism. $IC_{50}$ values determined from the graphs in FIGS. 4A-B were used to obtain combination index values: CI = [$IC_{50}$(carnosic acid + turmeric)/$IC_{50}$(carnosic acid alone)] + [$IC_{50}$(carnosic acid + turmeric)/$IC_{50}$(turmeric alone)].

Inhibition of ATPase Activity

The enzymatic assay of ATPase (adenosine 5'-triphosphatase, EC 3.6.1.3) followed the Sigma Prod. No. A-7510 protocol (Sigma-Aldrich, St. Louis, Mo., USA). Agents (0.05 ml) were pipetted with ATPase (0.05 ml, 0.5 units/ml, Sigma-Aldrich, St. Louis, Mo., USA), mixed and equilibrated for 5 min at 37° C. Taussky-Shorr reagent (10 ml of 10% ammonium molybdate in 10 N $H_2SO_4$) was pipetted to 70 ml $H_2O$, 5 g of ferrous sulfate heptahydrate was added, and the volume was brought to 100 ml with $H_2O$. Test supernatant (0.5 ml) and $H_2O$ (0.5 ml) were mixed and incubated at 25° C., and the absorbance read at A660 nm.

To determine whether the Na+-K+-ATPase is involved in the mechanism of action of CA and curcumin, the ability of these agents to inhibit the in vitro activity of the purified enzyme was assayed. The results showed 50% inhibition, IC50 value, at a concentration of curcumin of ~2 µM, and CA, paclitaxel and digitoxin of <0.1 µM (FIG. 3B).

Statistical Analysis

For cell growth and real-time PCR assay, the data are expressed as mean+/−standard deviation. Control and treated cells were compared using the Student's t-test, For gene expression analysis, the samples were analyzed by AffyLima analysis. The statistical significance of differential expression was calculated using the empirical Bayesian LIMMA (LI Model for MicroArrays) method of Smyth et al. (Smyth, G. K. et al., "Use of within-array replicate spots for assessing differential expression in microarray experiments." Bioinformatics 2005; 21:2067-75, incorporated herein by reference): B=log e(odds of differential expression), the Bayesian natural (base e) log of the odds that the genes are differentially expressed.

The invention disclosed herein includes: 1) CA or compounds related to CA are potent inhibitors of breast cancer cell growth; 2) rosmarinic acid is less potent than CA or compounds related to CA; 3) the presence of Her2 increases the activity of CA; 4) extracts of rosemary and CA arrest the cell cycle at the G1 phase at low concentrations and G2 at high concentrations; 4) CA induces anti-inflammatory, oxidoreductase, apoptosis and glutathione metabolism genes and represses inhibtors of transcription and cell cycle genes; 5) CA synergizes with turmeric/curcumin on triple negative breast cancer cells; 6) CA and curcumin, as well as digitoxin, inhibit the activity of the purified Na+-K+-ATPase.

There are two major signaling pathways in breast cancer cells: the ER-mediated signaling pathway, present in the estrogen-dependent human breast cancer cell line MCF-7, and the HER2-mediated signaling pathway, present in the estrogen-independent human breast cancer cell line MDA-MB-453, which overexpresses HER2 (erb2, c-neu), encoding a membrane-associated tyrosine kinase receptor (p185 HER2). A reciprocal relationship often occurs in the expression of these two pathways in primary human breast cancer in clinical studies. Therefore, the effect of CA on the two cell types was compared and it was found that sensitivity correlates with Her2 expression, as shown in FIG. 2A. CA is thus especially suited to prevent and treat Her2 overexpressing breast cancer, the harder to treat breast cancer. Since studies indicate that Her2 has the ability to expand the stem/progenitor cell population and make it more tumorigenic and invasive, CA can have the potential to inhibit the growth of breast cancer stem cells.

CA arrests the cell cycle at the G1 phase and suppresses the expression of the G1 cell cycle gene CDKN2C. As disclosed herein, rosemary extract/CA contains a mixture of components with the more active (or more abundant) component causing G1 arrest and the less active causing G2 arrest and/or individual component(s) in the extract exert different effects at different concentrations. It is likely that high concentrations rosemary extract/CA affects proteins that regulate later phases in the cell cycle.

Studies in human leukemia cells indicate that CA activates the expression of phase 2 enzymes which mediate glutathione (the major cellular antioxidant) metabolism (GCLC, MRP) and transport which results in increased intracellular glutathione. The sustained stimulation of glutathione metabolism appears to remove reactive oxygen species. As disclosed herein, CA stimulates the expression of Phase 2 enzymes that are involved in glutathione metabolism in human breast cancer cells.

The invention disclosed herein, indicate that CA activates the expression two disparate sets of genes: 1) genes related to glutathione metabolism such as GCLC; and 2) aldoreductases such as AKR1C2. The study of Macleod (MacLeod, A. K. et al., "Characterization of the cancer chemopreventive NRF2-dependent gene battery in human keratinocytes: demonstration that the KEAP1-NRF2 pathway, and not the BACH1-NRF2 pathway, controls cytoprotection against electrophiles as well as redox-cycling compounds," Carcinogenesis 2009; 30:1571-80, incorporated herein by reference) explains the mechanism of induction of these two sets of genes. Knockdown of Keap 1 (in spontaneously immortalized human HaCaT keratinocytes) results in the activation of 23 mRNAs greater than 2-fold. The AKR family of drug metabolizing enzymes was the most upregulated (12-16-fold); while GCLC and HMOX1 were upregulated 2.4-8-fold. It is striking that when BACH1 is knocked down, HMOX1 is activated 135-fold, while other genes tested were upregulated up to 2.7-fold. Both these sets of genes share the presence of antioxidant response elements in their promoters. Redox and electrophilic stress alters the cysteine residues on KEAP1, which in turn inactivates KEAP1, thereby activates NRF2, which migrates to the nucleus and coordinately activates ARE-driven genes. HMOX1 has many copies of ARE-like sequences (MAF recognition elements) and appears to be induced by BACH1 protein. The finding that CA activates genes in the AKR family, as well as NRF2, correlates with the fact that some of these genes are upregulated in tumors; constitutive activation of NRF2 is observed in 20% of lung cancer patients.

It is important to develop novel therapeutic agents, which have an acceptable toxicity profile and activity against ER-negative breast cancer (about one-third of invasive breast cancers); triple negative breast cancer is especially difficult to treat. To reveal primary targets on triple negative breast cancer, the effects of CA were examined at an early time, 6 h, on MDA-MB-468 human breast cancer cells. CA activates more genes than it represses. At a low dose, CA activates the expression of 3 genes involved in glutathione metabolism and transport. At a higher dose CA activates the expression of 102 genes and represses 22 genes (ratio: 4.6/1). Since a ratio greater than one is characteristic of the response to stress, CA appears to induce a stress response.

To elucidate the signaling pathways altered by carnosic acid, triple negative breast cancer cells were treated with a higher dose. Among the altered genes at 20 g/ml, were: (activated) xenobiotic metabolism (AKR1C2), antioxidant (TNXRD1), anti-inflammatory (HMOX1) and apoptosis (GDF15, PHLDA1, DDIT3) genes and (suppressed) inhibitor of transcription (ID3) and cell cycle genes (CDKN2C). PCR analysis confirmed that CA activates the expression of the tumor suppressor gene, CDKN1A. Therefore CA, alone or in combination with other agents, also can prevent and treat inflammatory and oxidative diseases including cancer and cardiac disorders.

The effect of CA was examined on the gene that degrades vitamin D, CYP24A1 and a significant effect was found. The combination of CA and vitamin D can thus be an effective agent to prevent and treat triple negative breast cancer.

To uncover molecular targets, the effect of CA on the activity of the purified Na+-K+-ATPase was tested and it was found that CA and curcumin, as well as paclitaxel and digitoxin, inhibited its activity. Cardiac glycosides bind to the alpha subunit of the Na+-K+-ATPase, an oligomeric complex with two non-covalently linked catalytic subunits and a third subunit comprised of seven FXYD transmembrane proteins. Ouabain potently inhibits the enzyme's active transport of Na+ and K+ across cell membranes. The binding of ouabain also converts the enzyme to a signal transducer. This releases and activates Src, which subsequently phosphorylates effectors such as the epidermal growth factor receptor and activates signaling pathways such as Ras/Raf/ERK1/2 and phosphatidylinositol-3-OH-kinase (PI3K)/Akt/NF-κB that are implicated in cell survival. It is thus possible that CA and curcumin also release and activate SRC and downstream effectors that lead to growth inhibition.

The optimal treatment for breast cancer most likely requires a combination of agents or modalities. The studies of Pesakhov et al. (Pesakhov, S. et al. "Distinct combinatorial effects of the plant polyphenols curcumin, carnosic acid, and silibinin on proliferation and apoptosis in acute myeloid leukemia cells," Nutr Cancer 2010; 62:811-24, incorporated by reference herein) indicated that when AML cells are treated with combinations of low doses of curcumin and CA there was marked synergistic inhibition and enormous cell death by both extrinsic and intrinsic cell pathways. The components alone markedly increase glutathione levels at 4 and 8 h and the combination significantly increase the level at these times. To explain the synergy, Pesakhov et al. suggest that: 1) one component may stabilize another; 2) mutual stabilization due to antioxidant properties; 3) different phytochemicals may alter different pathways which converge on one target, such as activation of caspases; 4) one component may inhibit cellular mechanisms which mediate drug efflux. The later hypothesis is supported by studies, which indicate that CA inhibits the activity of the drug efflux transporter p-glycoprotein in human carcinoma KB-C2 cells.

To find optimal treatments for triple negative breast cancer, the effect of combinations of CA and curcumin were tested and the results showed significant synergy. Concentrations of CA that produce little inhibition of cell growth when tested alone can enhance the growth inhibitory effects of a dietary component used to prevent and treat breast cancer. The observed synergy of CA and turmeric also relates to: 1) the ability of these agents to inhibit the activity of the purified Na/K ATPase and to alter the ERK pathway; 2) indicates the two compounds bind to different active sites on the ATPase, or the binding of one compound enhances binding of the second agent; 3) the observation that CA and curcumin inhibit different phases of the cell cycle, G1 and S, respectively.

CA or its related compound is selective for breast cancer (e.g., Her2 overexpressing cells) and can inhibit the growth of cancer stein cells. CA potently inhibits the proliferation of triple negative human breast cancer. The combination of CA and curcumin or compounds related thereto, in particular, can prevent and treat triple negative breast cancer. This is especially attractive since rosemary/CA and turmeric/curcumin have a long history of safe use, and may have added health benefits beyond the potential for breast cancer treatment and prevention, such as for maintaining bone health and treating and preventing cardiovascular disease.

Growth Inhibitory Activity of Nanoparticle Carnosic Acid on Colon Cancer Cells and Breast Cancer Cells:

Nanoparticle Liposome Preparation

Fluorescent liposomes containing carnosic acid in the lipid bilayer were prepared by Encasula as below:

The liposomes are fusogenic and composed of DOPC:DOPE:Rhodamine-PE: Carnosic Acid (49.9:40:0.1:10 molar ratio).

The total lipid concentration is 10 mg/ml and the concentration of carnosic acid is 0.5 mg/ml in PBS buffer, pH 7.4, extruded through 100 nm polycarbonate membranes by high pressure nitrogen.

The nanoparticles can also be prepared using other diterpene compounds such as carnosol or other natural phenol antioxidant carboxylic acid such as rosmarinic acid.

The nanoparticles can also be prepared using other types of lipid such as 1,2-Dimyristoyl-sn-glycero-3-phosphocholine (DMPC) and (DMPC/DMPG) (DMPG=1,2-dimyristoyl-sn-glycero-3-[phospho(1-glycerol)] [sodium salt]). Yet further lipids that can be used include: lecithin (phosphatidylcholine); cholesterol, DLPC, DMPC, DPPC, DSPC, DOPC, DMPE, DOPE, DMPA-Na, DPPA-Na, DOPA-Na, DMPG-Na, DPPG-Na, DOPG-Na, DMPS-Na, DPPS-Na, DOPS-Na, DOPE-Glutaryl-(Na)$_2$, Tetramyristoyl Cardiolipin-(Na)$_2$, DSPE-mPEG-2000-Na, DSPE-mPEG-5000-Na, DSPE-Maleimide-PEG-2000-Na, DOTAP-Cl. In addition to the specifically listed PEGylated lipids, polyethylene glycol can be added to any lipid or combination of lipids used to make the liposomes of the invention. PEGylated liposomes will be prepared as described in: Lin Y-Y, Kao H-W, Li J-J, Hwang J-J, Tseng Y-L, et al. (2013) Tumor Burden Talks in Cancer Treatment with PEGylated Liposomal Drugs. PLoS ONE 8(5): e63078. doi:10.1371/journal.pone.0063078 incorporated herein by reference.

The ratio of total lipid to compound (weight/weight) can range from 10:1 to 4:1. For combinations, the lipo-carnosic acid and lipo-chemotherapeutic agent will also be mixed using a 3-way adjuvant mixer (Narayanan et al., 2009). See Li et al., 2005 for liposome preparation.

This agent and method (lipsomes) can also be used to prepare combinations of diterpenes or natural phenol antioxidant carboxylic acid with chemopreventive and chemotherapy agents such as paclitaxel, doxorubicin, 5-FU, Herceptin, tamoxifen, sulindac sulfide, turmeric.

Proliferation Assay of Liposome-Encapsulated Carnosic Acid

HT29 (p53 positive human colon cancer cells), as well as MDA-MB-453 Her2 overexpressing ER-negative human breast cancer cells are treated with increasing concentrations of the liposome carnosic acid complex and carnosic acid.

It is clear that in accord with our invention liposomes increase the activity of carnosic acid.

Colon cancer cells: Treatment of HT29 human colon cancer cells with carnosic acid at 1 µg/ml resulted in 99.3% proliferation, whereas liposome-carnosic acid at 1 µg/ml resulted in 57.7% proliferation.

Breast cancer cells: Treatment of MDA-MB-453 human breast cancer cells with carnosic acid at 0.5 µg/ml resulted in 107% proliferation, whereas liposome-carnosic acid at 0.5 g/ml resulted in 64.9% proliferation; treatment with carnosic acid at 2 µg/ml resulted in 98.9% proliferation, whereas liposome-carnosic acid at 2 µg/ml resulted in 86.3% proliferation; treatment with carnosic acid at 5 µg/ml resulted in 91.5% proliferation, whereas liposome-carnosic acid at 5 µg/ml resulted in 76.6% proliferation.

Thus, concentrations of CA (0.5 µg/ml) that produce no inhibition of cell growth when tested alone can significantly inhibit the growth (35%) when encapsulated in liposomes. Cells were exposed to increasing concentrations of agents for 96 h and the number of viable cells determined by the MTT assay. The results are depicted in Table 4.

TABLE 4

Growth inhibitory Effect of Carnosic Acid and Liposome-Carnosic acid on MDA-MB-453 breast cancer cells Proliferation

| Concentration (ug/ml) | Carnosic Acid | Liposome-Carnosic Acid |
| --- | --- | --- |
| 0 | 1 | 1 |
| 0.5 | 1.07 | 0.649 |
| 2 | 0.989 | 0.863 |
| 5 | 0.915 | 0.766 |
| 10 | 0.758 | 0.677 |
| 20 | 0.573 | 0.506 |

Growth Inhibitory Activity of Rosemary, Carnosic Acid and Turmeric on Ovarian Cancer Cells:

SKOV3 (Her2 overexpressing) ovarian cancer cells (ATCC, Manassas, Va.), were grown in McCoy's media (Gibco BRL Life Technologies, Inc., Rockville, Md.) containing 10% (v/v) fetal bovine serum (FBS) (Gibco BRL) at 37° C., 5% $CO_2$, plus Penn-Strep (Sigma).

MTT Assay:

The MTT [3-(4,5-dimethyl-2-thiazol)-2,5-diphenyl-2H tetrazolilum bromide] (Dojindo; Tokyo, Japan) cell proliferation assay system (Roche Diagnostic, Mannheim, Germany) was used to determine the sensitivity of the cell lines to agents. Cells were seeded at $1 \times 10^4$ cells/well in 96-well plates and allowed to attach for 24 h. The medium was replaced with fresh medium containing DMSO or compound. The cells were treated for 96 h, after which the media was replaced with fresh media; the cells were incubated with MTT reagents and the absorbance read at 650 and 575 nm. The 650 reading was subtracted from the 575 reading to correct for background absorbance.

Figure 6:
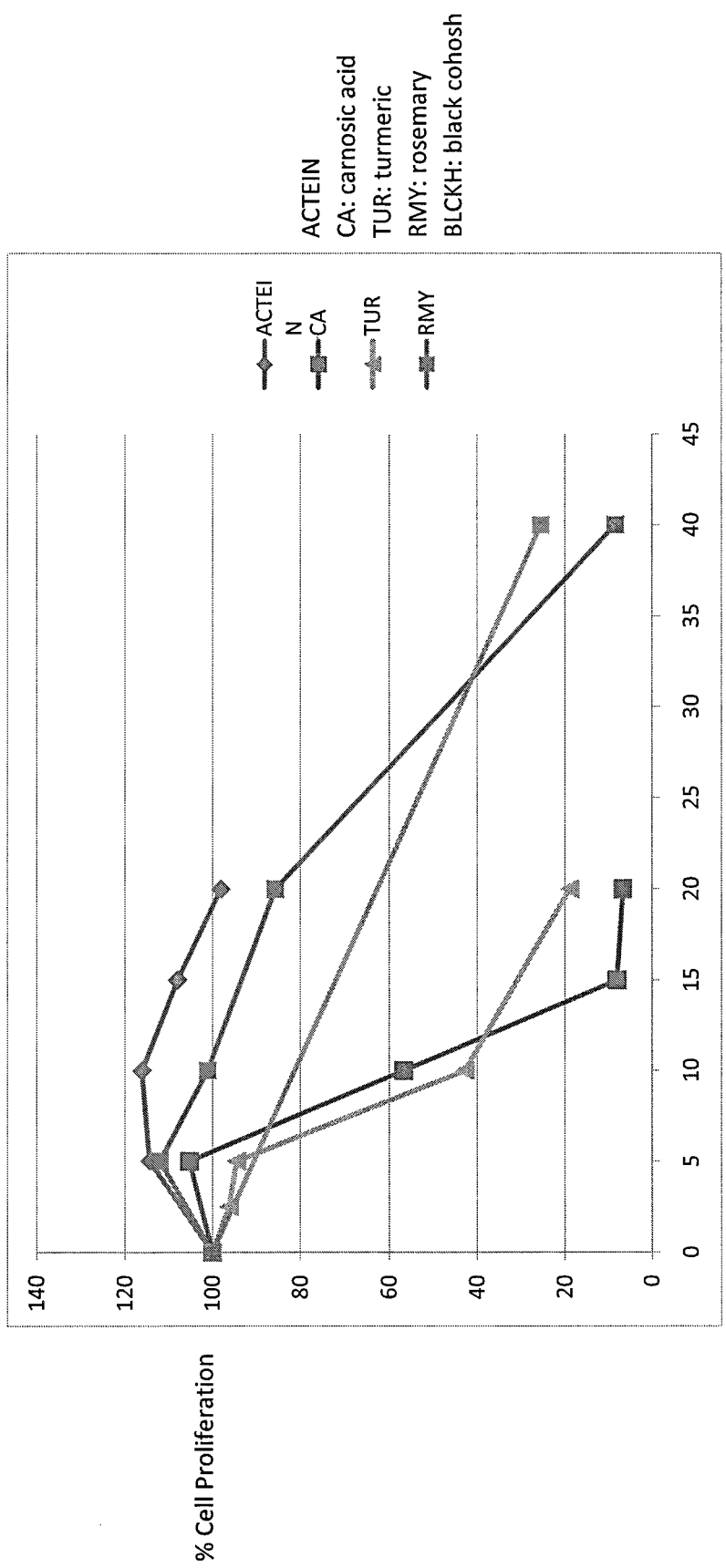
FIG. 6 is a graph growth inhibitory activity of rosemary, carnosic acid and turmeric on ovarian cancer cells.

The growth inhibitory activity of rosemary extract, enriched for carnosic acid (50%), carnosic acid and turmeric (95% curcuminids) was examined on SKOV3 (Her2 overexpressing) human ovarian cancer cells (FIG. 6). The $IC_{50}$ values, the concentration that caused 50% inhibition of cell growth, was approximately 9 µg/ml for turmeric, 10.5 µg/mL (31.6 µM) for carnosic acid and 30 µg/ml for rosemary on SKOV3 ovarian cancer cells cancer cells. Thus turmeric (TUR) and carnosic acid (CA) displayed strong growth inhibitory activity on SKOV3 human ovarian cancer cells, followed by rosemary extract (RMY) and then black cohosh extract (BLCKH; 27% triterpene glycosides) and actein (ACT).

FIG. 6 shows % cell proliferation as a function of concentration (µg/ml) after SKOV3 cells were exposed to various agents for 96 h. Result values are also shown below in Table 5.

TABLE 5

| ACT (µg/ml) | % | CA (µg/ml) | % | TUR (µg/ml) | % | RMY (µg/ml) | % | BLCKH (µg/ml) | % |
| --- | --- | --- | --- | --- | --- | --- | --- | --- | --- |
| 0 | 100 | 0 | 100 | 0 | 100 | 0 | 100 | 0 | 100 |
| 5 | 114.4 | 5 | 105.3 | 2.5 | 96.2 | 5 | 112.0 | 40 | 25.4 |
| 10 | 116.1 | 10 | 56.7 | 5 | 94.5 | 10 | 101.4 | | |
| 15 | 108.0 | 15 | 8.1 | 10 | 42.8 | 20 | 85.7 | | |
| 20 | 98.1 | 20 | 6.7 | 20 | 18.9 | 40 | 8.5 | | |

Therefore, rosemary/carnosic acid and turmeric/curcumin can be used to prevent (i.e., inhibit development of) and treat ovarian cancer.

Exosomes

Isolation of microvesicles (MV):

Microvesicles can be categorized based on size, site of origin and mechanism of formation as either microparticles (100 nm-1 um) or exosomes (30-100 nm).

Microvesicles (exosomes+microparticles) were isolated from animal cells using the protocol I sent earlier today (below).

Figure 7:
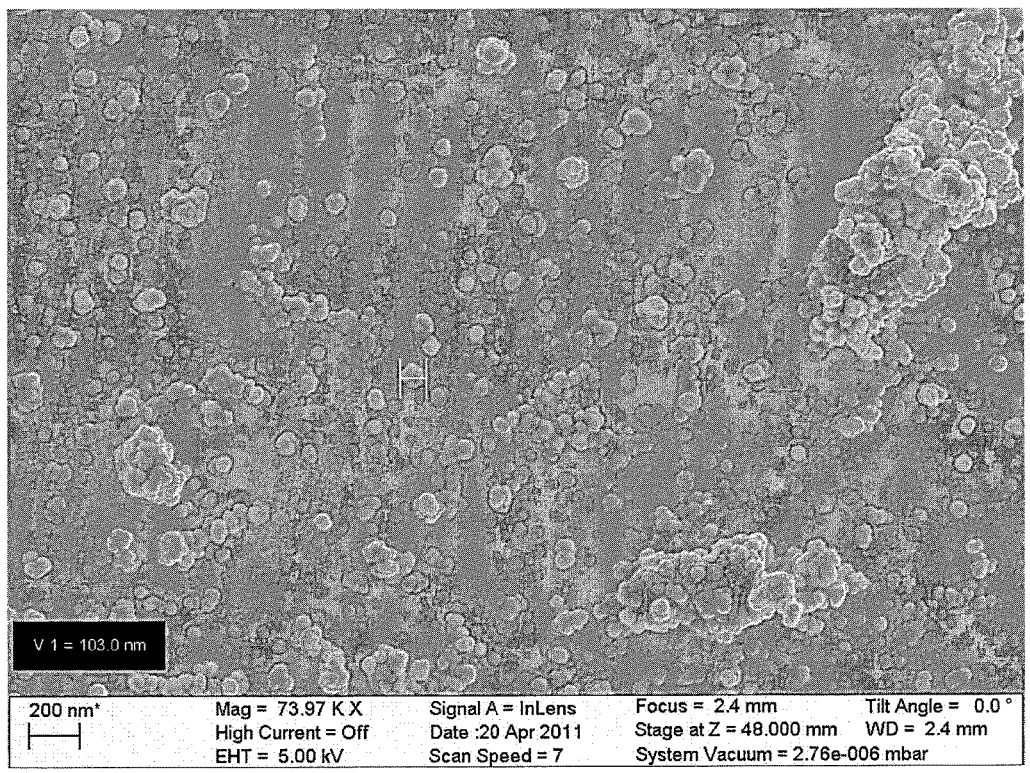
FIG. 7 is photograph of a scanning electron micrograph (SEM) image of isolated microvesicles.

Isolated microvesicles (exosomes+microparticles) were prepared from animal cells according to the modified protocol proposed by Yuan, A., et al. (Transfer of microRNAs by embryonic stem cell microvesicles. PLoS One. 2009; 4(3):e4722. PubMed PMID: 19266099. Pubmed Central PMCID: 2648987. Epub 2009/03/07. eng.) incorporated herein by reference. About 24-48 hours after plating, the media was collected and transferred into centrifuge tubes (polypropylene conical bottom) and centrifuged at 3500 g for 30 min at 4° C. to pellet debris and fragmented cells. The supernatant was carefully transferred to an ultracentrifuge tube and spun at 100,000 g for 2 hours in a Beckman Ultracentrifuge (rotor 60ti) at 4° C. to pellet the microvesicles. SEM Analysis of Cell derived exosomes and microparticels. Total MV populations isolated from cells include a heterogenous population of spheroid vesicles ranging in size from 30-300 nM (FIG. 7).

Exosomes will be purified from the microvesicle samples using the methods of Lasser et al. (J Vis Exp. 2012; (59): 3037. Published online 2012 Jan. 9. doi: 10.3791/3037 PMCID: PMC3369768, Isolation and Characterization of RNA-Containing Exosomes) incorporated herein by reference.

Similar methods will be used to isolate exosomes from plants. Exosomes from rosemary (leaves) and turmeric (rhizomes) will be prepared and, optionally, also mixed with purified carnosic acid (Sigma, St. Louis, Mo.) or curcumin (LKT laboratories, St. Paul, Minn.) (purity>90%), respectively, to enrich for these components (Sun et al., 2010) (as described in James Graham Brown Cancer Center; clinical trial: NCT01294072, BCC-GI-10 Curcumin; Feb. 3, 2011). Carnosic acid and curcumin will be characterized by HPLC compared with standards (Naturex, South Hackensack, N.J.).

What is claimed is:

1. A method of treating breast cancer or inhibiting development of breast cancer comprising administering a pharmaceutically effective amount of a composition comprising carnosic acid in liposomes comprising lipids to a breast cancer patient in need thereof or to a patient at risk of developing breast cancer, wherein said composition comprises DOPC:DOPE:Rhodamine-PE:carnosic acid having a molar ratio of 49.9:40:0.1:10.

2. A method of treating breast cancer or inhibiting development of breast cancer comprising administering a pharmaceutically effective amount of a composition comprising carnosic acid in liposomes comprising lipids to a breast cancer patient in need thereof or to a patient at risk of developing breast cancer, wherein said composition comprises DOPC:DOPE:Rhodamine-PE:carnosic acid having a molar ratio of 49.9:40:0.1:10, and wherein said breast cancer is characterized by the presence of Her2.

* * * * *